(12) United States Patent
Gross et al.

(10) Patent No.: US 8,554,302 B2
(45) Date of Patent: Oct. 8, 2013

(54) APPARATUS HAVING A COMBINED MAGNETIC RESONANCE APPARATUS AND RADIATION THERAPY APPARATUS

(75) Inventors: Patrick Gross, Langensendelbach (DE); Björn Heismann, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 224 days.

(21) Appl. No.: 13/023,914

(22) Filed: Feb. 9, 2011

(65) Prior Publication Data
US 2011/0196226 A1    Aug. 11, 2011

(30) Foreign Application Priority Data

Feb. 10, 2010 (DE) .......................... 10 2010 001 743

(51) Int. Cl.
*A61N 5/00* (2006.01)
*A61B 5/055* (2006.01)

(52) U.S. Cl.
USPC ........................................................ 600/411

(58) Field of Classification Search
USPC ......... 600/411, 427, 407, 422, 415, 421, 410, 600/425; 378/65, 147, 156, 63, 144, 8, 19, 378/64, 45; 324/218, 309, 307; 601/4
See application file for complete search history.

(56) References Cited

U.S. PATENT DOCUMENTS

| | | | |
|---|---|---|---|
| 6,198,957 B1 | 3/2001 | Green | |
| 2008/0208036 A1* | 8/2008 | Amies et al. | 600/411 |
| 2009/0234219 A1 | 9/2009 | Kruip | |

FOREIGN PATENT DOCUMENTS

| | | |
|---|---|---|
| DE | 696 33 033 T2 | 7/2005 |
| DE | 698 30 480 T2 | 3/2006 |
| DE | 10 2008 007 245 A1 | 9/2008 |
| DE | 20 2008 014 892 U1 | 5/2009 |
| GB | 2 393 373 A | 3/2004 |
| WO | WO 03/008986 A2 | 1/2003 |
| WO | WO 2009/106603 A1 | 9/2009 |

* cited by examiner

*Primary Examiner* — Long V. Le
*Assistant Examiner* — Lawrence Laryea

(57) ABSTRACT

An apparatus having a combined magnetic resonance apparatus is proposed. The magnetic resonance apparatus features at least one main magnet for generating a main magnetic field in an examination space for a magnetic resonance measurement, and a radiation therapy apparatus, which is provided to generate a particle beam and which features a beam guide. The magnetic resonance apparatus features an essentially magnetic-field-free region and the beam guide for the particle beam runs along the essentially magnetic-field-free region.

19 Claims, 3 Drawing Sheets

APPARATUS HAVING A COMBINED MAGNETIC RESONANCE APPARATUS AND RADIATION THERAPY APPARATUS

CROSS REFERENCE TO RELATED APPLICATIONS

This application claims priority of German application No. 10 2010 001 743.4 filed Feb. 10, 2010, which is incorporated by reference herein in its entirety.

FIELD OF THE INVENTION

The present invention relates to an apparatus having a combined magnetic resonance apparatus, which features at least one main magnet for generating a main magnetic field in an examination space for a magnetic resonance measurement, and radiation therapy apparatus, which is provided to generate a particle beam and features a beam guide.

BACKGROUND OF THE INVENTION

In the context of radiation therapy a target within a human body generally has to be irradiated in order to treat a disease for example, in particular a tumor. In this process a radiation therapy apparatus applies a high radiation dose in a targeted manner in an irradiation region (isocenter) of the human body. During irradiation the problem frequency occurs that the irradiation region moves and/or is displaced. Thus a tumor in a stomach region for example moves during an respiratory process of a patient. On the other hand a tumor can grow or reduce in size in a time interval between radiation planning and the actual irradiation.

It has therefore been proposed to monitor a position of an irradiation target in a patient during irradiation by means of medical imaging. This allows a beam and/or beam guide for irradiation to be controlled or optionally irradiation to be terminated. It is also of significant interest to track a radiation focus in respect of the actual position of the irradiation region.

A combined radiation therapy apparatus and magnetic resonance apparatus is particularly advantageous. This features high soft part resolution compared with a computed tomography apparatus for example, so that an advantageous contrast can be shown in this region.

For efficient irradiation a radiation source of the radiation therapy apparatus is positioned as close as possible to a patient. To this end the radiation source is generally disposed at least partially within the magnetic resonance apparatus and in particular within a magnetic field of the magnetic resonance apparatus. However this arrangement has the disadvantage that an electron path of electrons of an electron beam of the radiation therapy apparatus is subject to interference from the magnetic field of the magnetic resonance apparatus.

WO 03/008986 A2 proposes a separation of gradient coils of the magnetic resonance apparatus and a tailored design of a main magnet, so that an almost magnetic-field-free space is produced outside the magnetic resonance apparatus. However this arrangement has the disadvantage that the apparatus is of large extension and only one angle of incidence is available for a radiation treatment. Also the separated gradient coils result in significant disadvantages in respect of the image quality of medical imaging. Also the radiation from the radiation therapy apparatus must penetrate a steel body of the magnet, resulting in a deterioration and/or degradation of the beam profile and beam intensity.

A combined magnetic resonance apparatus and radiation therapy apparatus, in which however an x-ray and/or gamma beam is generated for the purposes of irradiation outside the magnetic resonance apparatus and therefore outside the active region of a magnetic field, is also known from U.S. Pat. No. 6,198,957 B1. This means that the x-ray beam is generated a very long distance from the actual treatment region, so the apparatus is likewise of large extension, in particular with a variation of an angle of incidence. Also the long distance means that a high radiation dose has to be generated, to achieve the required penetration depth of radiation for the radiation treatment.

A guide for an electron beam along a main axis of the magnetic resonance apparatus is also known from DE 102008007245 A1. The electron beam is deflected through 90° to collide with a target. An electron beam and the target are disposed within a patient support of the magnetic resonance apparatus. However this means that the space available for the patient within the magnetic resonance apparatus is additionally limited by the radiation therapy apparatus.

SUMMARY OF THE INVENTION

The object of the present invention is in particular to provide an apparatus with a combined magnetic resonance apparatus and radiation therapy apparatus, which provides a compact structure and high quality image monitoring by means of magnetic resonance measurement during radiation therapy. The object is achieved by the features of the independent claims. Further advantageous embodiments are described in the subclaims.

The invention is based on an apparatus having a combined magnetic resonance apparatus, which features at least one main magnet for generating a main magnetic field in an examination space for a magnetic resonance measurement, and a radiation therapy apparatus, which is provided to generate a particle beam and features a beam guide.

It is proposed that the magnetic resonance apparatus should feature an essentially magnetic-field-free region and that the beam guide for the particle beam should run along the essentially magnetic-field-free region. In this context a main magnetic of the magnetic resonance apparatus is understood in particular to be a magnet that is provided to apply and/or generate a constant and in particular homogeneous main magnetic field. The main magnet is preferably formed by a superconducting magnet. Also a magnetic-field-free region is understood in particular to be a region in which overlaid magnetic fields neutralize one another essentially mutually, so that a resulting main magnetic field is essentially canceled out. The essentially magnetic-field-free region can feature a residual magnetic field, the strength of the residual magnetic field being much lower than the strength of the main magnetic field. An examination space is also understood in particular to be a space and/or region of the magnetic resonance apparatus, which is provided to receive a patient and in which an imaging examination and/or measurement is performed on the patient by means of the magnetic resonance apparatus and irradiation is performed by means of the radiation therapy apparatus. A radiation therapy apparatus is understood in particular to be an apparatus which is provided to irradiate a region, for example a tumorous region of a patient, with an ionizing, high-energy radiation, the ionizing, high-energy radiation acting on the patient from the outside. The ionizing, high-energy radiation is predominantly formed by a gamma radiation and/or an x-ray radiation and/or an electron radiation, with the energy of the radiation being matched to a tissue type within the treatment region and/or a position of the treatment region within the patient and in particular beneath the skin of the patient. Irradiation with neutrons and/or protons and/or heavy ions by means of the radiation therapy apparatus is also possible. A particle beam is also understood in this context in particular to be a directed movement of a plurality of particles along a uniform preferred direction, such as a stream of particles with an essentially uniform flight direction for example. A beam guide here can in particular be formed by a predetermined radiation profile of the particle beam.

The inventive apparatus advantageously allows an apparatus to be achieved with a compact structure, in that the radiation therapy apparatus can be disposed in a particularly space-saving manner at least partially within the magnetic resonance apparatus. Also unwanted interference with imaging measurement, as could be caused by interference with the homogeneity of the main magnetic field by the particle beam, is reduced and/or prevented, so that high-quality image monitoring by means of a magnetic resonance measurement can be achieved during radiation therapy. Also a magnetic resonance apparatus with a high-field magnetic field can be used, as any adverse effect on the magnetic resonance apparatus and radiation therapy apparatus is prevented. Also unwanted interference with beam guidance by the applied main magnetic field can be suppressed due to the arrangement of the beam guide in the magnetic-field-free region.

The beam guide preferably runs outside a receiving region of the magnetic resonance apparatus, with the receiving region being provided to receive a patient, with the result that the receiving region can be made available to the patient without restriction, so that anxiety states, in particular due to patient claustrophobia inside the receiving region, can be suppressed during a measurement.

A particularly compact arrangement, in which the radiation therapy apparatus can be integrated at least partially in a space-saving manner in the magnetic resonance apparatus, can be achieved if the beam guide for the particle beam runs at least partially within the main magnet along the essentially magnetic-field-free region. For an at least partial integration of the radiation therapy apparatus within the main magnet a main magnet is particularly advantageously suitable, which is formed by a superconducting magnet configured as a minimum helium magnet. Such a minimum helium magnet preferably does not require cooling in a helium bath. Instead windings of a magnetic field coil of the main magnet are cooled directly using small quantities of helium. There is then no need to embed the minimum helium magnet in an overall cryostat assembly as is normal for superconducting magnets of a magnetic resonance apparatus and the minimum helium magnet can be disposed in a vacuum vessel, that can be configured in a much more flexible manner and thereby prevents unwanted thermal bridges. The beam guide of the radiation therapy apparatus can be integrated in a particularly space-saving manner within this vacuum vessel for example.

It is further proposed that the main magnet should feature a first magnetic field coil for generating a first magnetic field and at least one second magnetic field coil for generating a second magnetic field, with the beam guide running at least partially between the two magnetic field coils. The second magnetic field is preferably formed by a counter magnetic field that at least partially counteracts the first magnetic field, so that an at least partial cancellation and/or neutralization of the two magnetic fields can be achieved, in particular in a space between the two magnetic coils, thereby achieving an essentially magnetic-field-free region and/or space within the main magnet. The first magnetic field coil preferably has a diameter that is greater than a diameter of the at least second magnetic field coil, so that the at least one second magnetic field coil can be disposed in a space-saving manner within a region enclosed by windings of the first magnetic field coil.

The magnetic-field-free region between the two magnetic field coils preferably extends essentially along and/or parallel to the length of the two magnetic field coils so that the beam guide runs essentially parallel to the length between the two magnetic field coils.

It is also proposed that the beam guide should run at least partially parallel to a direction and/or orientation of a magnetic flux density of the main magnetic field. This allows an essentially magnetic-force-free beam guide to be achieved for the particle beam within the main magnet.

It is further proposed that the main magnet should feature at least two individual magnets, which are disposed together in a vacuum vessel. This allows advantageous cooling to be achieved whilst saving large quantities of helium and the beam guide to be disposed in a particularly space-saving manner within the main magnet.

In one advantageous development of the invention it is proposed that the beam guide should run along an at least partially curved trajectory within the main magnet. It is thus advantageously possible to compensate for a residual magnetic field present within the main magnet along the beam guide by a radius of curvature of the trajectory. Active and/or passive correction of a path of the particle beam is possible here, for example based on active beam deflection by local magnetic coils along the beam guide, etc.

It is also proposed that the radiation therapy apparatus should feature an accelerator unit, which is disposed at least partially within the magnetic resonance apparatus, the accelerator unit advantageously being formed by a linear accelerator unit. This allows a particularly compact arrangement of the accelerator unit to be achieved within the apparatus. This can be achieved advantageously, if the linear accelerator unit is disposed at least partially within the main magnet.

In this context a linear accelerator unit (linac) is understood in particular to be a unit for the acceleration of electrically charged particles, in particular electrons, the particles being accelerated on a straight path. Acceleration of the particle beam takes place here by means of alternating electric fields in a cylindrical hollow conductor. The hollow conductor here is preferably disposed in a vacuum tube, thereby preventing unwanted collisions of the beam particles with air molecules and/or air particles. For radiation therapy electrons can be accelerated for example to energies up to the order of a number of MeV. It is also possible for the radiation therapy apparatus to feature an alternative accelerator unit to the linear accelerator unit.

The accelerator unit can also feature a vacuum vessel separate from the vacuum vessel of the main magnet. This allows for example unwanted absorption of the particle beam, in particular beta absorption of electrons of the particle beam, at the vacuum vessel of the main magnet to be prevented during the entry and/or exit of the particle beam into the main magnet.

It is also proposed that the accelerator unit should be disposed at least partially within a vacuum vessel of the main magnet. This allows further components and in particular the costs of a separate vacuum vessel and/or a separate vacuum unit of the radiation therapy apparatus to be dispensed with.

It is also proposed that the main magnet should feature a vacuum vessel having at least one entry and/or exit window, through which the particles of the particle beam can enter the vacuum vessel and/or leave the vacuum vessel again. The entry and/or exit window here is preferably formed from a material that only interacts to a minor degree with the particle beam, so that when the particle beam strikes the entry and/or exit window any loss of beam intensity and/or beam guidance deviation and/or beam widening can be reduced and/or prevented. It is possible to at least reduce or prevent unwanted beam deflection and/or scattering of particles of the particle beam as the particle beam enters and/or exits the vacuum vessel.

In a further embodiment of the invention it is proposed that the radiation therapy apparatus should feature at least one target element, which is disposed within a vacuum vessel of the radiation therapy apparatus and/or the main magnet, it being possible in this process to achieve a particularly space-saving arrangement and/or positioning of the target within the magnetic resonance apparatus. It is also possible to achieve a space-saving arrangement in proximity to a patient and thus particularly close to a treatment region. The electrons of the electron beam of the linear accelerator striking the target element are slowed down at the target element and in the process emit a braking radiation formed by the high-energy photons. The target element here can be formed by a transmission target element or a reflection target element.

An advantageous irradiation of a treatment region from different irradiation angles can be achieved if the radiation therapy apparatus features at least one target element, which is formed by a target ring around a receiving region of the magnetic resonance apparatus. To this end the radiation therapy apparatus preferably features at least two or more beam guides, which are disposed within the magnetic resonance apparatus and in particular within the main magnet and which can be used depending on the irradiation angle selected. The radiation therapy apparatus can also provide a beam guide, which essentially has the form of a cylindrical sleeve surface within the main magnet, allowing bombardment of the target ring and/or the striking of the target ring by the particle beam over a selected partial angle range.

It is further proposed that the radiation therapy apparatus should feature at least one collimator element, which is disposed within a vacuum vessel of the radiation therapy apparatus and/or the main magnet. It is thus possible to achieve a particularly space-saving arrangement and/or positioning of the collimator element within the magnetic resonance apparatus and also a space-saving arrangement in proximity to the treatment region and thus particularly close to the patient. The collimator element is provided in particular to align the gamma and/or x-ray radiation of a gamma and/or x-ray beam in a parallel manner. In this process photons with an orientation away from the parallel radiation direction are preferably filtered out of the photon beam.

It is also proposed that the radiation therapy apparatus should feature at least one collimator element, which is disposed in such a manner that it can be moved about at least one axis and/or along at least one axis. This allows a gamma and/or x-ray beam to be given a desired beam profile and/or be applied to a desired treatment region for radiation therapy. To this end the at least one collimator element can particularly advantageously be tilted and/or rotated about an axis.

Particularly advantageous irradiation, in particular from different irradiation positions, of an irradiation region in a patient can be achieved if the radiation therapy apparatus features at two beam guides for the particle beam and the at least two beam guides are disposed within the magnetic resonance apparatus. A beam guide can be selected here based on a desired incidence position. Also the at least two beam guides can be used for simultaneous irradiation from different irradiation angles. A particularly compact arrangement can be achieved if the at least two beam guides for the particle beam are disposed at least partially within the main magnet.

It is further proposed that the beam guide should be disposed in such a manner that it can be displaced together with the at least partial magnetic resonance apparatus along at least one direction. This allows advantageous positioning of the particle beam and/or gamma and/or x-ray beam to be achieved in respect of the treatment region. A compact embodiment of the apparatus can also be retained and/or a powerful main magnetic field can be maintained for a magnetic resonance measurement during irradiation from different irradiation positions. It is also particularly advantageous for the beam guide to be disposed in such a manner that it can be displaced at least partially together with the magnetic resonance apparatus along two or three spatial directions, the spatial directions preferably being aligned orthogonally to one another.

It is also proposed that the beam guide should be disposed in such a manner that it can be rotated together with the at least partial magnetic resonance apparatus about at least one axis. The axis preferably runs through the receiving region for the patient, so that efficient irradiation of the patient, in particular of the treatment region of the patient, can be achieved from different angle positions.

The magnetic resonance apparatus particularly advantageously features a patient couch to move a patient into a receiving region, the patient couch being disposed in such a manner that it can be displaced along at least two directions. It is thus possible to achieve effective positioning of the patient in respect of the alignment and/or orientation of the particle beam and/or the gamma and/or x-ray beam of the radiation therapy apparatus.

It is also proposed that the particle beam and a gamma and/or x-ray beam generated from the particle beam should be aligned essentially orthogonally to one another. This allows an advantageous incident position of a treatment beam to be achieved in respect of the position of the patient and in particular in respect of a treatment region within the patient. The treatment beam can in particular be directed onto the patient essentially perpendicular to a head-foot axis of the patient in this process.

The magnetic resonance apparatus is particularly advantageously formed by a high field magnetic resonance apparatus, so that high quality signals can be achieved for the recorded magnetic resonance measurements. The magnetic field here preferably has a magnetic field strength of at least 3 Teslas and advantageously at least 5 Teslas.

BRIEF DESCRIPTION OF THE DRAWINGS

Further advantages will emerge from the description of the drawing which follows. The drawing illustrates exemplary embodiments of the invention. The drawings, description and claims contain numerous features in combination. The person skilled in the art will expediently consider the features individually as well and combine them in useful further combinations. In the drawing:

DETAILED DESCRIPTION OF THE INVENTION

Figure 1:
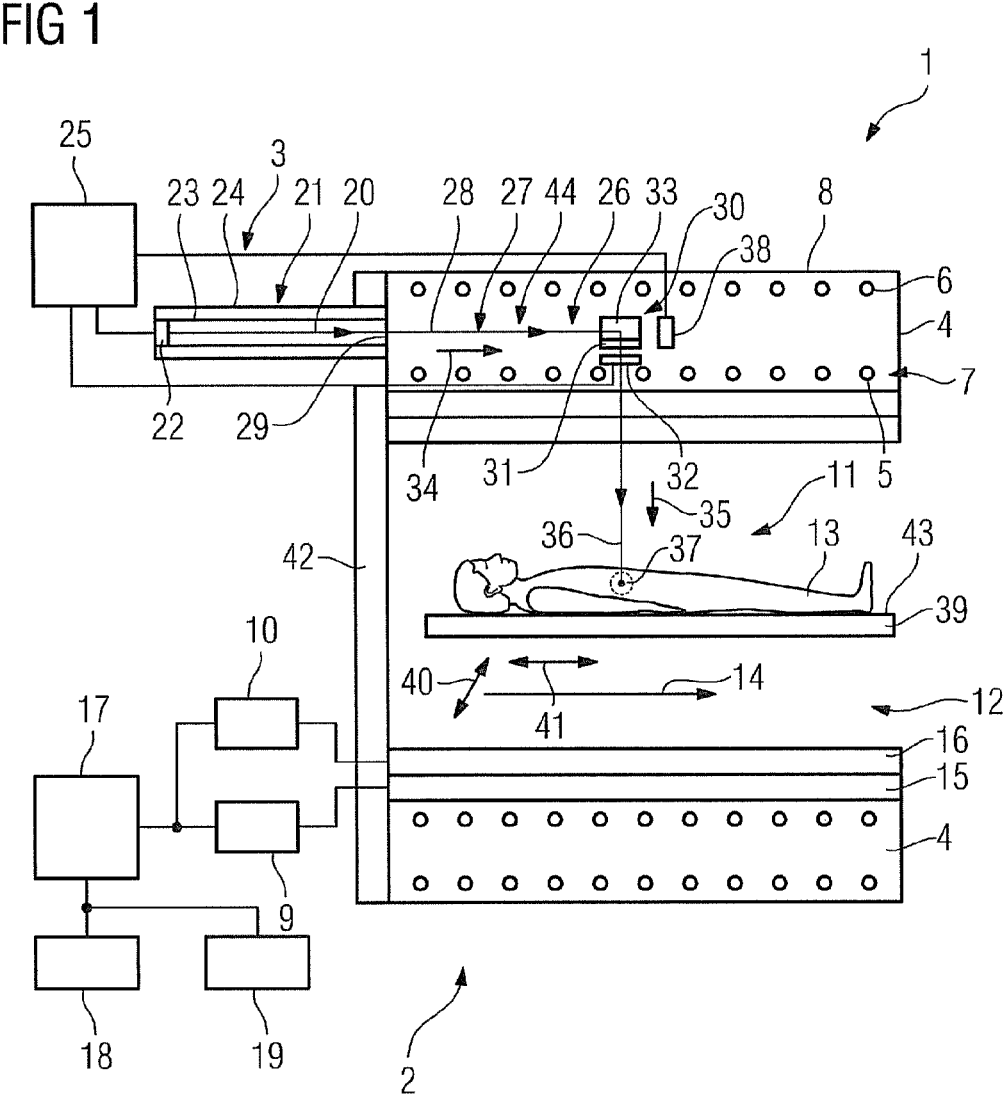
FIG. 1 shows a schematic diagram of an inventive apparatus.
Figure 2:
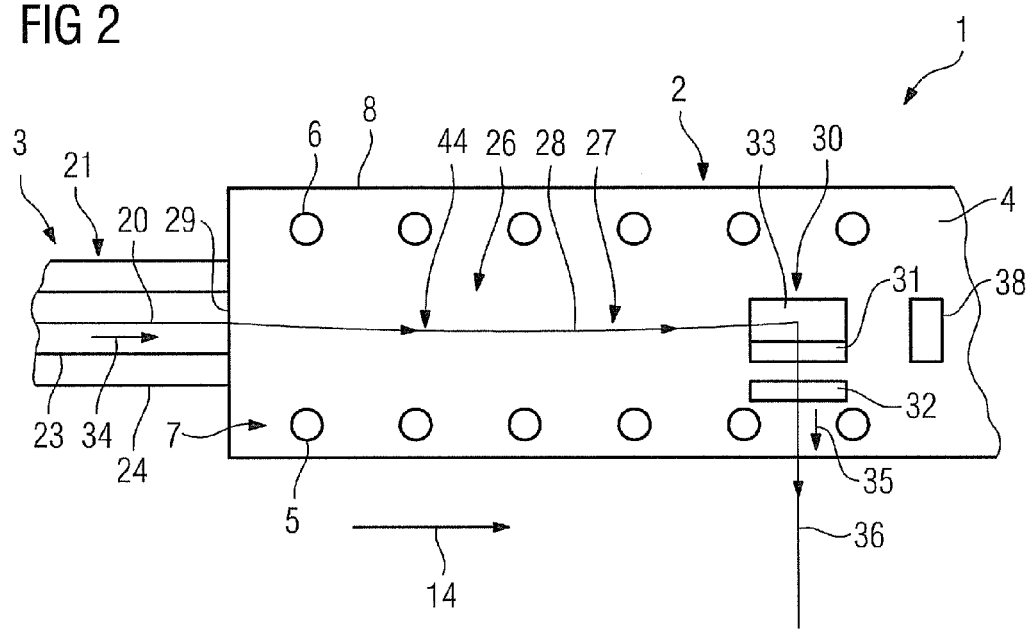
FIG. 2 shows a schematic diagram of a detailed view inside the apparatus from FIG. 1.

FIGS. 1 and 2 show an apparatus 1 having a combined magnetic resonance apparatus 2 and radiation therapy apparatus 3. The magnetic resonance apparatus 2 is formed by a high field magnetic resonance apparatus and comprises a main magnet 4, which is provided to generate an in particular homogeneous and constant main magnetic field during operation of the magnetic resonance apparatus 2. To this end the main magnet 4 is formed by a high field magnetic resonance magnet and comprises at least two magnetic field coils 5, 6, which are formed in particular by superconducting magnetic field coils 5, 6. One of the two magnetic field coils 5 is formed by a primary coil, which features a number of winding levels 7 and which is provided to generate the homogeneous magnetic field (FIG. 2). The further magnetic field coil 6 is formed by a stray field counter coil. The primary coil features a winding cross section that is smaller than the winding cross section of the stray field counter coil, so that the primary coil is disposed within the stray field counter coil.

In the present example the main magnet 4 is formed by a minimum helium magnet. This comprises a single vacuum vessel 8, in which the two magnetic field coils 5, 6 are disposed. Instead of the magnetic field coils 5, 6 being cooled in a helium bath, there is a small quantity of helium within the vacuum vessel 8, which is provided to cool windings of the two magnetic field coils 5, 6 directly.

The magnetic field generated by the main magnet 4 acts in an examination space 11 of the magnetic resonance apparatus 2, the examination space 11 being formed essentially by a receiving region 12 for receiving a patient 13 for a magnetic resonance measurement (FIG. 1). The orientation and/or direction of a magnetic flux density 14 of the main magnetic field here runs essentially perpendicular to a winding cross section of the two magnetic field coils 5, 6. The homogeneous main magnetic field is also essentially concentrated on the receiving region 12 enclosed by the magnetic field coils 5, 6.

The magnetic resonance apparatus 2 further comprises a gradient unit 15 for generating magnetic field gradients (FIG. 1). The gradient unit 15 features gradient coils (not shown in detail), which apply magnetic gradient fields for selective layer excitation and/or local coding of magnetic resonance signals along three spatial directions. A high frequency coil unit 16 is provided to stimulate polarization in the main magnetic field of the magnetic resonance apparatus 2 generated by the main magnet 4. Said high frequency coil unit 16 radiates a high frequency field, for example in the form of an HF pulse, into the patient 13, to deflect magnetization from an equilibrium position. The high frequency coil unit 16 can be used to record magnetic resonance signals from the examination space 11 in a measurement operation. The magnetic resonance apparatus 2 further comprises a gradient amplifier 9 to control the gradient coils and a high frequency amplifier 10 to control high frequency coils. To control the gradient amplifier 9 and the high frequency amplifier 10 the magnetic resonance apparatus 2 comprises a control unit 17. The control unit 17 controls the magnetic resonance apparatus 2 centrally, as for example in the automatic carrying out of a selected imaging gradient echo sequence. The control unit 17 controls the magnetic resonance apparatus 2 centrally, as for example in the automatic carrying out of a selected imaging gradient echo sequence. For the inputting of magnetic resonance parameters the magnetic resonance apparatus 2 comprises an input unit 18. The magnetic resonance apparatus 2 further comprises a display unit 19, which can be used to display magnetic resonance images for example.

The radiation therapy apparatus 3 is provided to generate a particle beam 20 during operation. To this end the radiation therapy apparatus 3 features an accelerator unit, which is formed by a linear accelerator unit 21. The linear accelerator unit 21 is configured as an electron accelerator unit. In principle an alternative embodiment of the accelerator unit to the linear accelerator unit 21 and/or the electron accelerator unit is possible, for example a proton accelerator unit, etc.

The linear accelerator unit 21 comprises an electron source 22, for example a tungsten cathode, which produces free electrons. These electrons are then accelerated and the particle beam 20 formed by an electron beam is generated. To this end the linear accelerator unit 21 features a cavity resonator 23. Electric fields of standing electromagnetic waves are generated in the cavity resonator 23. Within the cavity resonator 23 a number of cells are disposed one behind the other, the length of the individual cells being selected so that the electric field of the standing wave of a cell is reversed as soon as an electron enters the next cell. This ensures a continuous acceleration of the electrons to an energy of several MeV. The linear accelerator unit 21 further comprises a vacuum vessel 24 formed by a vacuum tube, within which the cavity resonator 23 is disposed in such a manner that a vacuum is present in the individual cells of the cavity resonator 23. To control and/or regulate the linear accelerator unit 21 the radiation therapy apparatus 2 features a control unit 25.

A radiation therapy treatment by means of the radiation therapy apparatus 3 takes place at the same time as a magnetic resonance measurement by means of the magnetic resonance apparatus 2, so that the radiation therapy treatment can be tailored effectively to movement of the patient for example. To this end the radiation therapy apparatus 2 is integrated at least partially within the magnetic resonance apparatus 3. The radiation therapy apparatus 2 features a beam guide 44 for the electron beam, which runs here through the main magnet 4 of the magnetic resonance apparatus 2, the beam guide 44 for the electron beam running between a winding level of the primary coil and the stray field counter coil. During operation of the magnetic resonance apparatus 2 a magnetic field counter to the primary coil is generated in the stray field counter coil, so that a low magnetic field region 26 results between the primary coil and the stray field counter coil. This low magnetic field region 26 is fowled at least partially by an essentially magnetic-field-free region 27, with the beam guide for the electron beam running along the essentially magnetic-field-free region 27. The beam guide for the electron beam therefore runs outside the receiving region 12 of the magnetic resonance apparatus 2 for receiving the patient 13. The magnetic-field-free region 27 is essentially formed by an undulating surface that extends cylindrically between the two magnetic field coils 5, 6 of the main magnet 4.

The beam guide here runs essentially parallel to the magnetic flux density 14 of the main magnetic field, with the beam guide for the electron beam running along an at least partially curved trajectory 28. The at least partially curved trajectory 28 serves to compensate for a residual magnetic field along the beam guide. The beam guide and/or trajectory 28 also runs essentially parallel to the magnetic flux density 14 of the main magnetic field of the main magnet 4. The beam guide here can be actively deflected along the trajectory 28, for example by means of local coils, etc. Provision can also be made for passive deflection, whereby a residual magnetic field between the two coils along the trajectory 28 is used for deflection purposes. It is possible in this process to calculate any residual magnetic field present along the desired beam profile for example based on the applied magnetic field in the individual magnetic field coils 5, 6. The particle beam 20 can then be radiated at a corresponding angle of incidence into the residual magnetic field of the main magnet 4, with the residual magnetic field bringing about a deflection so that the particle beam 20 strikes a target unit 30 in a defined position.

The linear accelerator unit 21 of the radiation therapy apparatus 2 is disposed outside the main magnet 4 of the magnetic resonance apparatus 2. For the electron beam to enter the main magnet 4 and in particular its vacuum vessel 8, this latter has an entry window 29, the vacuum vessel 24 of the linear accelerator unit 21 being directly adjacent to the entry window 29. To prevent an interaction, in particular a deflection and/or scattering, of the electrons of the electron beam with the entry window 29 of the vacuum vessel 8, the entry window 29 is made of a material that is essentially transparent for the electrons of the electron beam.

The radiation therapy apparatus 2 further comprises a target unit 30, which comprises a target element 31, a collimator element 32 and a beam deflection unit 33. The target unit 30 is disposed along a direction 34 of a velocity of the accelerated electrons of the electron beam after the cavity resonator 23 of the linear accelerator unit 21. The target unit 30 is also disposed within the vacuum vessel 8 of the main magnet 4, so that unwanted beam deflection due to a collision of accelerated electrons of the electron beam with air molecules and/or air particles is prevented. Once the accelerated electrons of the electron beam have passed through the cavity resonator 23 and a subregion of the main magnet 4, they first meet the beam deflection unit 33. Here the electron beam is deflected through approx. 90° onto the target element 31, a direction 35 of the velocity of the electrons being directed onto the receiving region 12. To prevent further deflection of the electrons experiencing this due to the essentially perpendicular alignment of the direction 35 of the velocity of the electrons to the direction of the magnetic flux density 14 of the main magnetic field, the target element 31 is disposed directly after the beam deflection unit 33. The target element 31 is formed by a transmission target element, for example made from a tungsten sheet. The accelerated electrons are slowed down at the target element 31, with gamma radiation and/or x-ray radiation being generated in the process. A gamma and/or x-ray beam 36 is generated at the transmission target element, being at an angle of essentially 0° to the electron beam incident at the transmission target element 31. The arrangement of the beam deflection unit 22 and the target element 31 within the main magnet 4 means that these are configured with magnetic resonance compatibility and formed from a non-magnetizable material.

The collimator element 32 is disposed after the target element 21 along the direction 35 of the electron beam. The collimator element 32 is used to generate parallel gamma and/or x-ray radiation from the diffuse gamma and/or x-ray radiation and focus this on a treatment region 38 of the patient 13. This provides a parallel beam profile of the gamma and/or x-ray radiation with a small radiation focus for radiation therapy. The collimator element 32 is also disposed in such a manner that it can be moved about an axis, so that the radiation focus can be adjusted onto the treatment region 37, for example tumorous tissue. The collimator element 32 is controlled and/or adjusted by means of the control unit 25, it being possible for control parameters and/or adjustment parameters to be input for this purpose by an operator, for example a physician, by way of an input unit (not shown in detail). The collimator element 32 is likewise disposed within the main magnet 4 and to this end is configured with magnetic resonance compatibility and formed from a non-magnetizable material.

The radiation therapy apparatus 3 further comprises a monitoring unit 38. The monitoring unit 38 is used to monitor the beam quality of the gamma and/or x-ray beam 36 generated at the target element 31, for example with regard to radiation dose and/or radiation focus. The monitoring unit 38 is controlled by the control unit 25 of the radiation therapy apparatus 3. As soon as parameters of the gamma and/or x-ray beam 36 deviate from a predetermined value, the control unit 25 terminates the radiation treatment. To this end the monitoring unit 38 is disposed in proximity to the target element 31 within the vacuum vessel 8 of the main magnet 4 and after the target element 31 along the beam profile. The monitoring unit 38 is likewise configured with magnetic resonance compatibility and formed from a non-magnetizable material.

The apparatus 1 is also provided to track a radiation focus of the gamma and/or x-ray beam 36. Tracking may be necessary if for example the isocenter and/or treatment region 38 of the radiation treatment move(s) during the radiation treatment, for example due to respiration and/or movement of the patient 13. The isocenter and/or treatment region 38 may also have a greater extension than the extension of the radiation focus of the gamma and/or x-ray beam 36, so that it is necessary to track the gamma- and/or x-ray beam 36 for complete irradiation of tumorous tissue for example. Tracking is based on magnetic resonance recordings, which locate the treatment region. To track the radiation focus of the gamma and/or x-ray beam 36 in respect of movement and/or extension of the isocenter, the apparatus 1 offers two options. On the one hand the magnetic resonance apparatus 2 features a patient couch 39, which is provided to move the patient 13 into the receiving region 12 of the magnetic resonance apparatus 2. The patient couch 39 is configured with magnetic resonance compatibility and found from a non-magnetizable material. The patient couch 39 is also configured in such a manner that it can be moved along two spatial directions within the receiving region 12. The two spatial directions are formed by an x-direction 40 and a z-direction 41 and are aligned orthogonally to one another. The z-direction 41 is also aligned along a direction of an insertion process for inserting the patient couch 39 into the receiving region 12. The patient couch 41 can also be disposed in such a manner that it can be moved along a third spatial direction, which is formed by a y-direction, with the third spatial direction being aligned orthogonally to the first and second spatial directions.

A further option for tracking the gamma- and/or x-ray beam 36 in respect of the isocenter and/or treatment region 37 is for at least the linear accelerator unit 21 and the target unit 30 of the radiation therapy apparatus 3 to be disposed in such a manner that they can be moved together with at least the main magnet 4 of the magnetic resonance apparatus 2. The movement of the linear accelerator unit 21 and target unit 30 of the radiation therapy apparatus 3 here must take place together with at least the main magnet 4 of the magnetic resonance apparatus 2, so that the beam guide for the electron beam can always be disposed in the almost field-free region 27 of the main magnet 4. To this end the apparatus 1 has a positioning unit 42, which moves the linear accelerator unit 21 and the target unit 30 of the radiation apparatus 3 together with at least the main magnet 4 of the magnetic resonance apparatus 2 along the three spatial directions in relation to the patient 13 and/or the patient couch 39. Alternatively movement can also be possible along just one or two spatial directions.

Provision can also be made for further structural units and/or structural elements of the magnetic resonance apparatus 2 additionally to be moved by the positioning unit 42 together with the linear accelerator unit 21 and the target unit 30 along the three spatial directions to track the gamma and/or x-ray beam. Further structural units and/or further structural elements of the radiation therapy apparatus 3 can also be moved by the positioning unit 42 along the three spatial directions to track the gamma and/or x-ray beam.

The apparatus 1 also provides for irradiation of the treatment region 37 from different irradiation angles and/or from different irradiation positions. The irradiation angle here is formed by a three-dimensional spatial angle in relation to a couch surface 43 of the patient couch 39. To this end the linear accelerator unit 21 and the target unit 30 of the radiation therapy apparatus 3 are rotated together with at least the main magnet 4 of the magnetic resonance apparatus 2 about an axis by means of the positioning unit 42. The axis here runs through a center of the receiving region 12 essentially parallel to an insertion direction of the patient couch 39, so that the linear accelerator unit 21 and the target unit 30 can be rotated together with at least the main magnet 4 of the magnetic resonance apparatus 2 about the patient 13 and moved to a new irradiation position.

Alternatively it is possible for the linear accelerator unit 21 and the target unit 30 of the radiation therapy apparatus 3 and the main magnet 4 of the magnetic resonance apparatus 2 to be positioned in a fixed manner and for the patient couch 39 together with the patient 13 to be tilted about an axis to vary the irradiation angle. The axis is preferably formed by a longitudinal axis of the patient couch 39.

Figure 3:
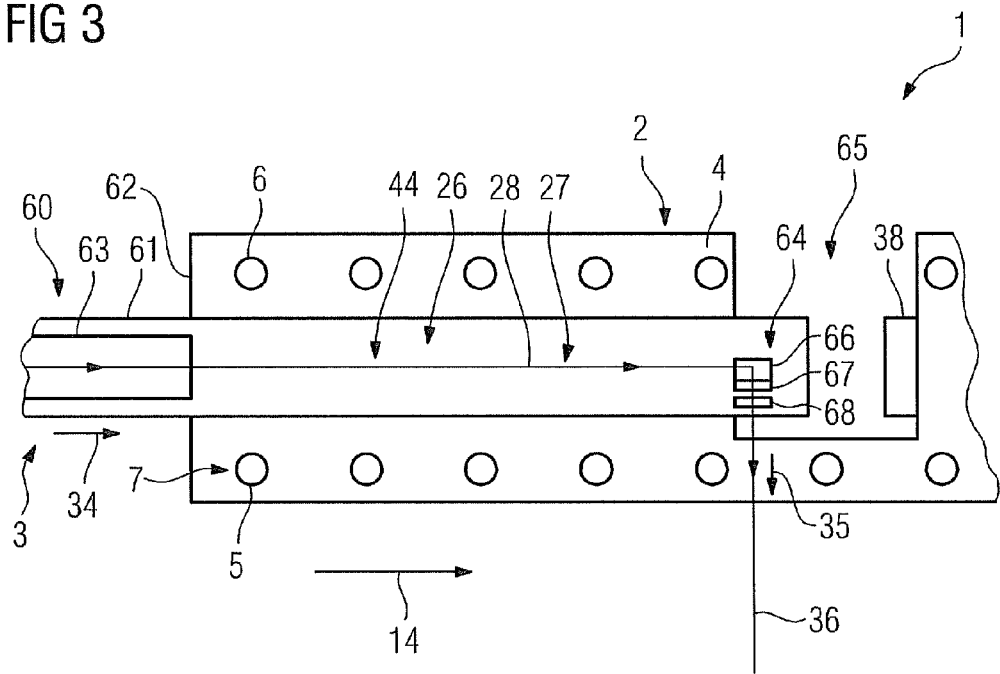
FIG. 3 shows a schematic diagram of an alternative embodiment of the apparatus.
Figure 4:
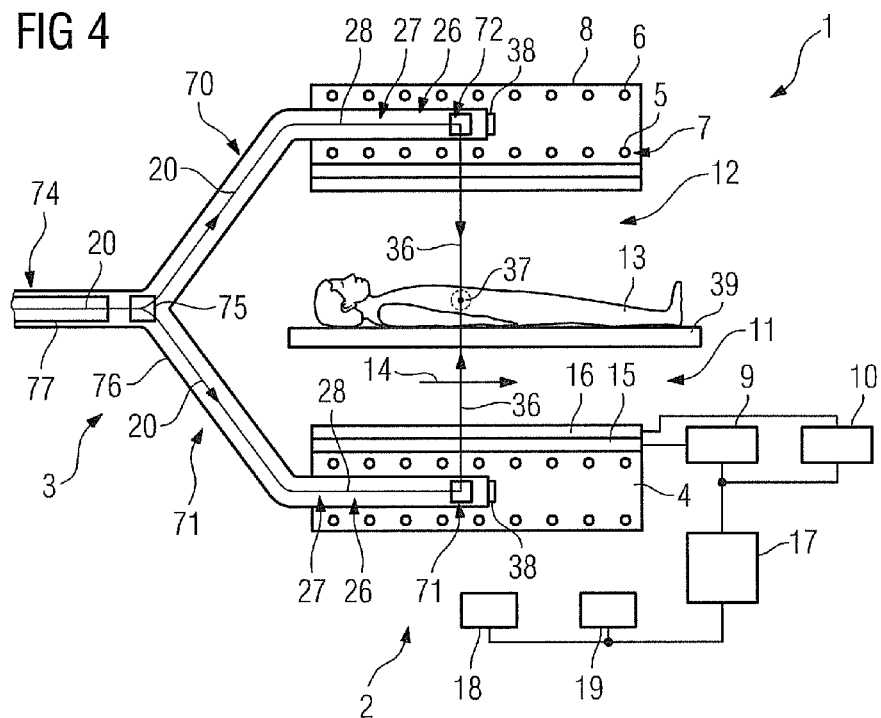
FIG. 4 shows a schematic diagram of an alternative embodiment of the apparatus with a number of beam guides and FIG. 5 shows a schematic diagram of an alternative embodiment of the apparatus with a target ring.
Figure 5:
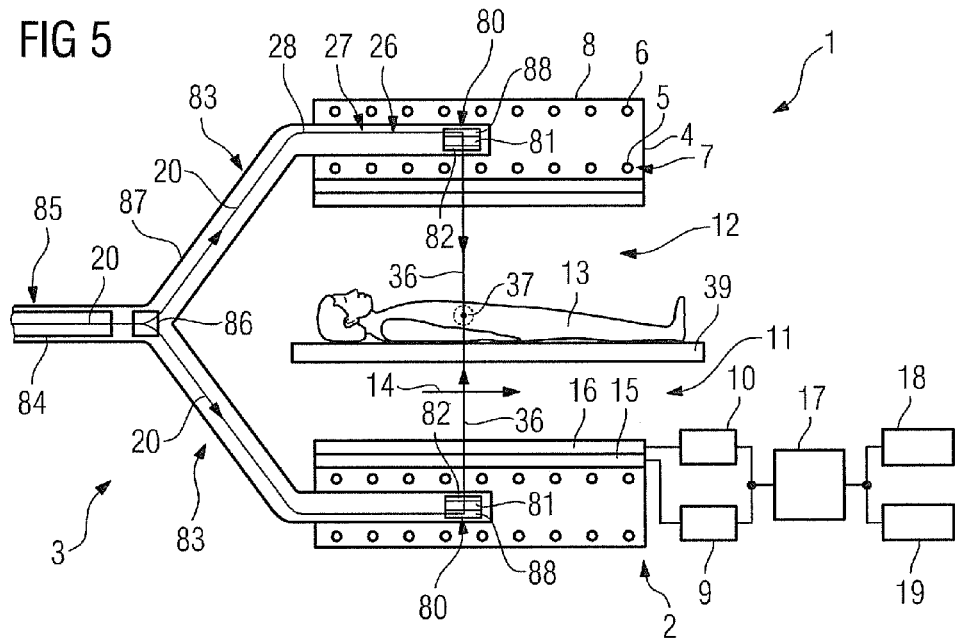

FIGS. 3 to 5 show alternative exemplary embodiments of the apparatus 1. Essentially identical components, features and functions are in principle marked with identical reference characters. The description which follows is essentially restricted to the differences compared with the exemplary embodiment in FIGS. 1 and 2, with reference being made to the description of the exemplary embodiment in FIGS. 1 and 2 for identical components, features and functions.

FIG. 3 shows an apparatus 1 having a combined magnetic resonance apparatus 2 and radiation therapy apparatus 3. The radiation therapy apparatus 3 comprises a linear accelerator unit 60 having a vacuum vessel 61, which is disposed within a main magnet 4 of the magnetic resonance apparatus 2. The vacuum vessel 61 of the linear accelerator unit 60 here extends through the essentially magnetic-field-free region 27 of the main magnet 4. A vacuum vessel 62 of the main magnet 4 is also embodied in such a manner that it encloses the vacuum vessel 61 of the linear accelerator unit 60 in a cylindrical manner along a beam direction of the particle beam 20. A cavity resonator 63 of the linear accelerator unit 60 is disposed within the vacuum vessel 61 of the linear accelerator unit 60 in a region of the vacuum vessel 61 outside the main magnet 4. The cavity resonator 63 is disposed in front of the main magnet 4 along a beam direction of the particle beam 20. An arrangement of the cavity resonator 63 within a region enclosed by the main magnet 4 is alternatively possible.

A target unit 64 of the linear accelerator unit 60 is disposed within the vacuum vessel 61 of the linear accelerator unit 60. The target unit 64 is also disposed outside the vacuum vessel 62 of the magnetic resonance apparatus 2. To this end the vacuum vessel 62 of the magnetic resonance apparatus 2 features a cutout 65, in which the target unit 64 is disposed, the vacuum vessel 61 of the linear accelerator unit 60 crossing the main magnet 4 up to the cutout 64 along the essentially magnetic field-free region 27. The target unit 64 comprises a beam deflection unit 66, a target element 67 and a collimator element 68, the mode of operation of the target unit 64 corresponding to the mode of operation of the target unit in FIGS. 1 and 2. When it leaves the collimator element 68 a gamma and/or x-ray beam 36 enters the vacuum vessel 62 of the main magnet 4 and crosses it essentially perpendicular to the magnetic flux density 14 of the main magnetic field and then enters the receiving region 12 for irradiation of the patient.

In a further alternative embodiment provision can further be made for the target unit 64 to be disposed within the vacuum vessel 62 of the main magnet 4 in which case there is no need for the cutout 65 in the vacuum vessel 62.

FIG. 4 shows a further alternative embodiment of the apparatus 1 having a combined magnetic resonance apparatus 2 and radiation therapy apparatus 3. The radiation therapy apparatus 3 features a number of beam guides 70, 71 for an electron beam, two of which are shown by way of example in FIG. 4. The beam guides 70, 71 are implemented within a main magnet 4 of the magnetic resonance apparatus 2. The individual beam guides 70, 71 run as described in relation to FIG. 1 between two magnetic field coils 5, 6 of the main magnet 4 in an essentially field-free region 27, the beam guides 70, 71 being aligned essentially parallel to a direction of a magnetic flux density 14 of the main magnetic field.

A cavity resonator 77 of a linear accelerator unit 74 is disposed outside the main magnet 4, with the different beam guides 70, 71 moving apart in a straight line from the cavity resonator 77, initially in a cone shape, and on reaching the main magnet 4 turning off into the magnetic-field-free region 27 of the main magnet 4. To this end deflection means (not shown in detail) for beam deflection along the beam guide 70, 71 for the accelerated particle beam 28 are disposed within the beam guides 70, 71.

The linear accelerator unit 74 also features a deflection unit 75, which deflects the electron beam into the selected beam guide 70, 71 after the cavity resonator 77. The deflection unit 75 of the linear accelerator unit 74 also provides for beam splitting of the particle beam 28, which splits the accelerated particle beam 28 according to a number of beam guides 70, 71. The resulting sub-beams can then be deflected and introduced into the respective beam guide 70, 71, to bring about simultaneous irradiation from different irradiation angles and/or irradiation positions. Each of the beam guides 70, 71 has a target unit 72, 73 of the radiation therapy apparatus 3 disposed within the magnetic resonance apparatus 2.

The target units 72, 73 are disposed within a vacuum vessel 76 of the linear accelerator unit 74. The target units 72, 73 and the vacuum vessel 76 of the linear accelerator unit 74 can also be disposed with the number of beam guides 70, 71 as described in relation to FIGS. 1 and 2 or as described in relation to FIG. 3.

FIG. 5 shows a further alternative embodiment of the apparatus 1 having a combined magnetic resonance apparatus 2 and radiation therapy apparatus 3. The radiation therapy apparatus 3 features a target unit 80 with a target element 81. The target element 81 here is formed by a target ring around a receiving region 12 of the magnetic resonance apparatus 2 and disposed within the main magnet 4. Disposed along the beam guide 83 in front of the target ring is a deflection ring 88 to deflect the beam of the particle beam 20. Also disposed along a beam guide 83 after the target ring is a collimator ring 82 to focus gamma and/or x-ray radiation generated at the target ring on a treatment region 37 of a patient 13. The beam guide 83 is configured in the manner of a cylindrical sleeve within the main magnet 4 and runs along an essentially magnetic-field-free region 27 of the main magnet 4. Outside the main magnet 4 the beam guide 83 runs outward from a cavity resonator 84 of a linear accelerator unit 85 in the direction of the main magnet 4 in the form of a straight cone surface. Disposed after the cavity resonator 84 is a deflection unit 86 of the linear accelerator unit 85, the mode of operation of which is as described in relation to FIG. 4. The target unit 81 is disposed within a vacuum vessel 87 of the linear accelerator unit 85. The target unit 81 and vacuum vessel 87 of the linear accelerator unit 85 can also be disposed with the beam guide 83 as described in relation to FIGS. 1 and 2 or as described in relation to FIG. 3.

Alternatively an electron beam can also be supplied to the target ring by way of a number of beam guides implemented within a main magnet 4 as described in relation to FIG. 4.

As an alternative to the exemplary embodiments described in FIGS. 1 to 5 it is also possible to dispense with a beam deflection unit within the target unit. However this requires a target element formed by a reflection target, whereby the incident electron beam and the outward gamma and/or x-ray beam form an angle that is essentially other than 0°.

As an alternative to the exemplary embodiments described in FIGS. 1 to 5 it is also possible for just one beam deflection unit and/or one target element of the target unit to be disposed within the vacuum vessel of the linear accelerator unit or within the vacuum vessel of the main magnet. A collimator element of the target unit here can be disposed outside the vacuum vessel of the linear accelerator unit or the vacuum vessel of the main magnet.

Also as an alternative to the exemplary embodiments described in FIGS. 1 to 5 a conventional superconducting magnet can be disposed within the main magnet, the windings of the individual magnetic field coils being cooled in a helium bath. The electron beam here would always take place in a vacuum vessel configured separately from the vacuum vessel of the main magnet. The main magnet can also be formed by a low field magnet or generate a low magnetic field.

The invention claimed is:

1. A magnetic resonance apparatus, comprising:
   a main magnet for generating a main magnetic field in an examination space for a magnetic resonance measurement, wherein the main magnetic field comprises a magnetic-field-free region, wherein the main magnet is disposed in a vacuum vessel;
   a radiation therapy apparatus for generating a particle beam; and
   a beam guide arranged in the radiation therapy apparatus and running at least partially within the vacuum vessel along the magnetic-field-free region for guiding the particle beam.

2. The apparatus as claimed in claim 1, wherein the main magnet comprises a first magnetic field coil for generating a first magnetic field and a second magnetic field coil for generating a second magnetic field, and wherein the beam guide runs at least partially between the first and the second magnetic field coils.

3. The apparatus as claimed in claim 1, wherein the beam guide runs at least partially parallel to a direction and/or orientation of a magnetic flux density of the main magnetic field.

4. The apparatus as claimed in claim 1, wherein the main magnet comprises at least two individual magnets that are disposed together in the vacuum vessel.

5. The apparatus as claimed in claim 1, wherein the beam guide runs along an at least partially curved trajectory within the main magnet.

6. The apparatus as claimed in claim 1, wherein the radiation therapy apparatus comprises an accelerator unit that is disposed at least partially within the magnetic resonance apparatus.

7. The apparatus as claimed in claim 6, wherein the accelerator unit is a linear accelerator unit.

8. The apparatus as claimed in claim 6, wherein the accelerator unit is disposed at least partially within the main magnet.

9. The apparatus as claimed in claim 6, wherein the accelerator unit comprises a vacuum vessel that is separate from a vacuum vessel of the main magnet.

10. The apparatus as claimed in claim 6, wherein the accelerator unit is disposed at least partially within a vacuum vessel of the main magnet.

11. The apparatus as claimed in claim 1, wherein the main magnet comprises a vacuum vessel with at least one entry and/or exit window.

12. The apparatus as claimed in claim 1, wherein the radiation therapy apparatus comprises a target element that is disposed within a vacuum vessel of the radiation therapy apparatus and/or the main magnet.

13. The apparatus as claimed in claim 1, wherein the radiation therapy apparatus comprises a target element that is a target ring around a receiving region of the magnetic resonance apparatus.

14. The apparatus as claimed in claim 1, wherein the radiation therapy apparatus comprises a collimator element that is disposed within a vacuum vessel of the radiation therapy apparatus and/or the main magnet, and wherein the collimator element is moved about an axis and/or along an axis.

15. The apparatus as claimed in claim 1, wherein the radiation therapy apparatus comprises at least two beam guides for the particle beam and the two at least beam guides are disposed at least partially within the main magnet.

16. The apparatus as claimed in claim 1, wherein the beam guide is displaced together with the magnetic resonance apparatus along a direction.

17. The apparatus as claimed in claim 1, wherein the beam guide is rotated together with the magnetic resonance apparatus about an axis.

18. The apparatus as claimed in claim 1, wherein the magnetic resonance apparatus is a high field magnetic resonance apparatus and comprises a patient couch for moving a patient into a receiving region and the patient couch is displaced along at least two directions.

19. The apparatus as claimed in claim 1, wherein the particle beam is aligned essentially orthogonally to a gamma and/or x-ray beam generated from the particle beam.

* * * * *